US010902334B2

(12) United States Patent
Letterie et al.

(10) Patent No.: US 10,902,334 B2
(45) Date of Patent: Jan. 26, 2021

(54) AUTOMATED IMAGE ANALYSIS TO ASSESS REPRODUCTIVE POTENTIAL OF HUMAN OOCYTES AND PRONUCLEAR EMBRYOS

(71) Applicants: Gerard Letterie, Seattle, WA (US); Andrew MacDonald, Seattle, WA (US)

(72) Inventors: Gerard Letterie, Seattle, WA (US); Andrew MacDonald, Seattle, WA (US)

(*) Notice: Subject to any disclaimer, the term of this patent is extended or adjusted under 35 U.S.C. 154(b) by 244 days.

(21) Appl. No.: 16/073,126

(22) PCT Filed: Jan. 30, 2017

(86) PCT No.: PCT/US2017/015645
§ 371 (c)(1),
(2) Date: Jul. 26, 2018

(87) PCT Pub. No.: WO2017/132674
PCT Pub. Date: Aug. 3, 2017

(65) Prior Publication Data
US 2019/0042958 A1 Feb. 7, 2019

Related U.S. Application Data

(60) Provisional application No. 62/288,379, filed on Jan. 28, 2016.

(51) Int. Cl.
G06K 9/00 (2006.01)
G06N 5/04 (2006.01)
(Continued)

(52) U.S. Cl.
CPC ......... G06N 5/045 (2013.01); G06K 9/00147 (2013.01); G06K 9/4604 (2013.01);
(Continued)

(58) Field of Classification Search
CPC .......... G06N 5/045; G06N 20/00; G06T 7/12; G06T 7/13; G16H 50/70; G16H 50/20;
(Continued)

(56) References Cited

U.S. PATENT DOCUMENTS

2010/0188496 A1* 7/2010 Xie ................... G01N 21/65
348/79
2011/0230362 A1* 9/2011 Craig ................ G16B 25/00
506/8
(Continued)

FOREIGN PATENT DOCUMENTS

| CN | 104462673 A | 3/2015 |
|---|---|---|
| JP | 2015130806 A | 7/2015 |

(Continued)

OTHER PUBLICATIONS

Extended European Search Report dated Sep. 13, 2019, issued in corresponding European Application No. 17745088.9, filed Jan. 30, 2017, 8 pages.
(Continued)

Primary Examiner — Stephen P Coleman
(74) Attorney, Agent, or Firm — Christensen O'Connor Johnson Kindness PLLC

(57) ABSTRACT

A computer system automatically converts a set of training images of cells (e.g., oocytes or pronuclear embryos) and related outcome metadata into a description document by extracting features (e.g., cytoplasm features) from the pixel values of the training images that describe the cells and associating the extracted features with the outcome metadata. Based on the description document, the system automatically computes a decision model that can be used to predict outcomes of new cells. To predict outcomes of new cells, a computer system automatically extracts features from images that describe the new cells and predicts one or more outcomes by applying the decision model. The features
(Continued)

extracted from the images that describe the new cells correspond to features selected for inclusion in the decision model, and are calculated in the same way as the corresponding features extracted from the training images.

27 Claims, 6 Drawing Sheets

(51) Int. Cl.
    *G06K 9/62*     (2006.01)
    *G16H 50/70*     (2018.01)
    *G16H 30/40*     (2018.01)
    *G06K 9/46*     (2006.01)
    *G06T 7/12*     (2017.01)
    *G16H 50/20*     (2018.01)
    *G06T 7/60*     (2017.01)
    *G06T 7/00*     (2017.01)
    *G06T 7/13*     (2017.01)
    *G06N 20/00*     (2019.01)

(52) U.S. Cl.
    CPC ......... *G06K 9/4633* (2013.01); *G06K 9/6256* (2013.01); *G06K 9/6262* (2013.01); *G06N 20/00* (2019.01); *G06T 7/0012* (2013.01); *G06T 7/0014* (2013.01); *G06T 7/12* (2017.01); *G06T 7/13* (2017.01); *G06T 7/60* (2013.01); *G16H 30/40* (2018.01); *G16H 50/20* (2018.01); *G16H 50/70* (2018.01); *G06T 2207/10056* (2013.01); *G06T 2207/20061* (2013.01); *G06T 2207/20081* (2013.01); *G06T 2207/30024* (2013.01)

(58) Field of Classification Search
    CPC ... G16H 30/40; G06K 9/00147; G06K 9/4604
    USPC ......................................................... 382/155
    See application file for complete search history.

(56) References Cited

U.S. PATENT DOCUMENTS

| | | | | |
|---|---|---|---|---|
| 2011/0254943 | A1* | 10/2011 | Ozinsky | G01N 21/6458 348/79 |
| 2013/0230230 | A1* | 9/2013 | Ajemba | G06K 9/00147 382/133 |
| 2014/0247972 | A1 | 9/2014 | Wang et al. | |

FOREIGN PATENT DOCUMENTS

| | | | |
|---|---|---|---|
| WO | 2014/089647 A1 | 6/2014 | |
| WO | 2015/161045 A1 | 10/2015 | |
| WO | 2015/189264 A1 | 12/2015 | |
| WO | WO-2015189264 A1 * | 12/2015 | ......... G06K 9/00147 |

OTHER PUBLICATIONS

Wu, Q., et al., "Microscope Image Processing," Jan. 1, 2008, Elsevier/Academy Press, Amsterdam, pp. v-xx.
Alvarez Sedó, A., et al., "Correlation Between Cytoplamic Oocyte Maturation and Chromosomal Aneuploidies—Impact on Fertilization, Embryo Quality and Pregnancy," JBRA Assisted Reproduction 19(2):59-65, May 2015.
Basile, T.M.A., et al., "A Texture-Based Image Processing Approach for the Description of Human Oocyte Cytoplasm," IEEE Transactions on Instrumentation and Measurement 59(10):2591-2601, Oct. 2010.
Campbell, A., et al., "Aneuploidy Is a Key Causal Factor of Delays in Blastulation: Author Response to a Cautionary Note Against Aneuploidy Risk Assessment Using Time-Lapse Imaging," Reproductive BioMedicine Online 28(3):279-283, Mar. 2014.
Ciray, H.N., et al., "Proposed Guidelines on the Nomenclature and Annotation of Dynamic Human Embryo Monitoring by a Time-Lapse User Group," Human Reproduction 29(12):2650-2660, Dec. 2014.
International Search Report dated Apr. 21, 2017, issued in corresponding International Application No. PCT/US2017/15645, filed Jan. 30, 2017, 3 pages.
Lazzaroni-Tealdi, E., et al., "Oocyte Scoring Enhances Embryo-Scoring in Predicting Pregnancy Chances With IVF Where It Counts Most," PLoS ONE 10(12):e0143632, Dec. 2015, pp. 1-13.
Santos Filho, E., et al., "A Method for Semi-Automatic Grading of Human Blastocyst Microscope Images," Human Reproduction 27(9):2641-2648, Sep. 2012.
Santos Filho, E., et al., "A Review on Automatic Analysis of Human Embryo Microscope Images," Open Biomedical Engineering Journal 4:170-177, Oct. 2010.
Sterckx, S., et al., "Patenting Medical Diagnosis Methods in Europe: Standard University and Time-Lapse Microscopy," Reproductive BioMedicine Online 34(2):166-168, Feb. 2017.
Sterckx, S., et al., "Patenting Time-Lapse Microscopy: The European Story," Reproductive BioMedicine Online 28(2):146-150, Feb. 2014.
Vera-Rodriguez, M., et al., "Prediction Model for Aneuploidy in Early Human Embryo Development Revealed by Single-Cell Analysis," Nature Communications 6:7601, Jul. 2015, pp. 1-14.
Written Opinion dated Apr. 21, 2017, issued in corresponding International Application No. PCT/US2017/15645, filed Jan. 30, 2017, 5 pages.
Wu, Y.-G., et al., "Different Effectiveness of Closed Embryo Culture System With Time-Lapse Imaging (EmbryoScope™) in Comparison to Standard Manual Embryology in Good and Poor Prognosis Patients: A Prospectively Randomized Pilot Study," Reproductive Biology and Endocrinology 14(1):49, Aug. 2016, pp. 1-11.
Zhang, B., and T.D. Pham, "Phenotype Recognition With Combined Features and Random Subspace Classifier Ensemble," BMC Bioinformatics 12:128, Apr. 2011, pp. 1-13.
Office Action dated Oct. 6, 2020, filed Jan. 30, 2017, in corresponding Japanese application No. 2018-559173, 8 pages.
"Medical applications of image processing technology", [online], Nov. 26, 2015, [Sep. 25, 2020 search, Internet < URL:https://shingi.jst.go.jp/past_abst/abst/p/15/tus/tus05.pdf>.

* cited by examiner

AUTOMATED IMAGE ANALYSIS TO ASSESS REPRODUCTIVE POTENTIAL OF HUMAN OOCYTES AND PRONUCLEAR EMBRYOS

CROSS-REFERENCE TO RELATED APPLICATION

This application claims the benefit of U.S. Provisional Application No. 62/288,379, filed Jan. 28, 2016, the disclosure of which is hereby incorporated by reference herein.

BACKGROUND

Conventional assessment of embryo quality is performed through static, daily measurements by observers using traditional bright field examination of embryos during 5 days of development. Though a variety of scoring systems can be used to translate these observations into semi-quantifiable scores, selection of the embryo or embryos most likely to implant remains a qualitative exercise. This process is labor and cost intensive, requires considerable training and skill, and may be impacted by factors common to any repetitive technique of observation such as fatigue and inter- and intra-observer variability.

Conventionally, oocytes are retrieved and immediately sorted based only on maturity or immaturity, with the former being inseminated. Performance of these oocytes awaits an expensive and time consuming routine of culturing over 5 days.

Manual oocyte scoring may provide useful clinical information. However, manual assessment of oocytes and embryos remains standard of care and has not changed significantly since inception of human embryology techniques. Thus, there remains a need for better tools to assess the reproductive potential of oocytes and pronuclear embryos to identify those with a high likelihood of developing into blastocysts and ultimately a live birth.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a computer system automatically converts a set of training images of cells (e.g., oocytes or pronuclear embryos) and related outcome metadata into a description document by extracting features from the pixel values of the training images and associating the extracted features with the outcome metadata. Then, based on the description document, the computer system automatically computes a decision model that can be used to predict outcomes of new cells. The training images are obtained using bright-field microscopy.

The extracted features may include a boundary of a cytoplasm. The computer system may detect such boundaries in the training images by applying an edge detection algorithm to the images to detect edges and applying a circle detection algorithm to the detected edges to detect an approximate cytoplasm boundary. The computer system may convert color images to grayscale images prior to application of the edge detection algorithm. After the approximate cytoplasm boundary is detected, the computer system may create an annular mask image from the approximate cytoplasm boundary and perform image segmentation on the original source image to identify a connected region as the cytoplasm.

Additional extracted features may include one or more of the following: total area of the cytoplasm; aspect ratio of the cytoplasm; convexity of the boundary of the cytoplasm; average image intensity of the cytoplasm; standard deviation of the image intensity of the cytoplasm; smoothness of the cytoplasm; subsampled image intensity or smoothness for grid areas within the cytoplasm; cytoplasmic texture or texture distribution; density; and clustering. The average image intensity of the cytoplasm may be calculated by averaging the corresponding pixel values of the identified cytoplasm in a grayscale image.

For oocytes or pronuclear embryos, additional extracted features may include one or more of the following: a boundary of a polar body, measured manually or with image analysis using an edge detection algorithm; an indication as to whether the polar body exists; identification of inner and outer edges of a zona pellucida; identification of perivitelline space; a measurement of smoothness of the edges of the zona pellucida; alignment of principal axes of the cytoplasm and the zona; total area of the polar body, the zona pellucida, or the perivitelline space; aspect ratio of the polar body, the zona pellucida, or the perivitelline space; convexity of a boundary of the polar body, the zona pellucida, or the perivitelline space; average image intensity of the polar body, the zona pellucida, or the perivitelline space; standard deviation of the image intensity of the polar body, the zona pellucida, or the perivitelline space; smoothness of the polar body, the zona pellucida, or the perivitelline space; and subsampled image intensity or smoothness for grid areas within the polar body, the zona pellucida, or the perivitelline space.

For pronuclear embryos, additional extracted features may include one or more of the following: identification of the boundaries of the pronuclei, measured manually or with image analysis using an edge detection algorithm; area of the pronuclei, measured individually and/or relative to each other; aspect ratio of the pronuclei, measured individually and/or relative to each other; convexity of a boundary of one or more of the pronuclei; average image intensity of one or more of the pronuclei; standard deviation of the image intensity of one or more of the pronuclei; smoothness of one or more of the pronuclei; and subsampled image intensity or smoothness for grid areas within one or more of the pronuclei.

In another aspect, a computer system automatically extracts features from new cell images (which, like the training images, also may be obtained using bright-field microscopy) that describe the new cells and predicts one or more outcomes for the new cells by applying the decision model to the features extracted from the new cell images. The features extracted from the new cell images correspond to features of the training images selected for inclusion in the decision model, and may be calculated for in the same way. The outcomes may include one or more of quality or reproductive potential for a new oocyte, whether abnormalities in chromosome number are detected later in development, whether genetic disorders are detected later in development, and abnormal cell growth outcomes. The quality or reproductive potential for a new oocyte may be expressed as one or more of: a probability that the oocyte will fertilize when exposed to human sperm, a probability that a resulting embryo will reach a given stage of development, or a probability that the resulting embryo will result in a live birth when transferred to a uterus.

These functions may be implemented as an add-on to an existing image analysis system or as a separate system. The system may be integrated with a microscopy system for obtaining cell images.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
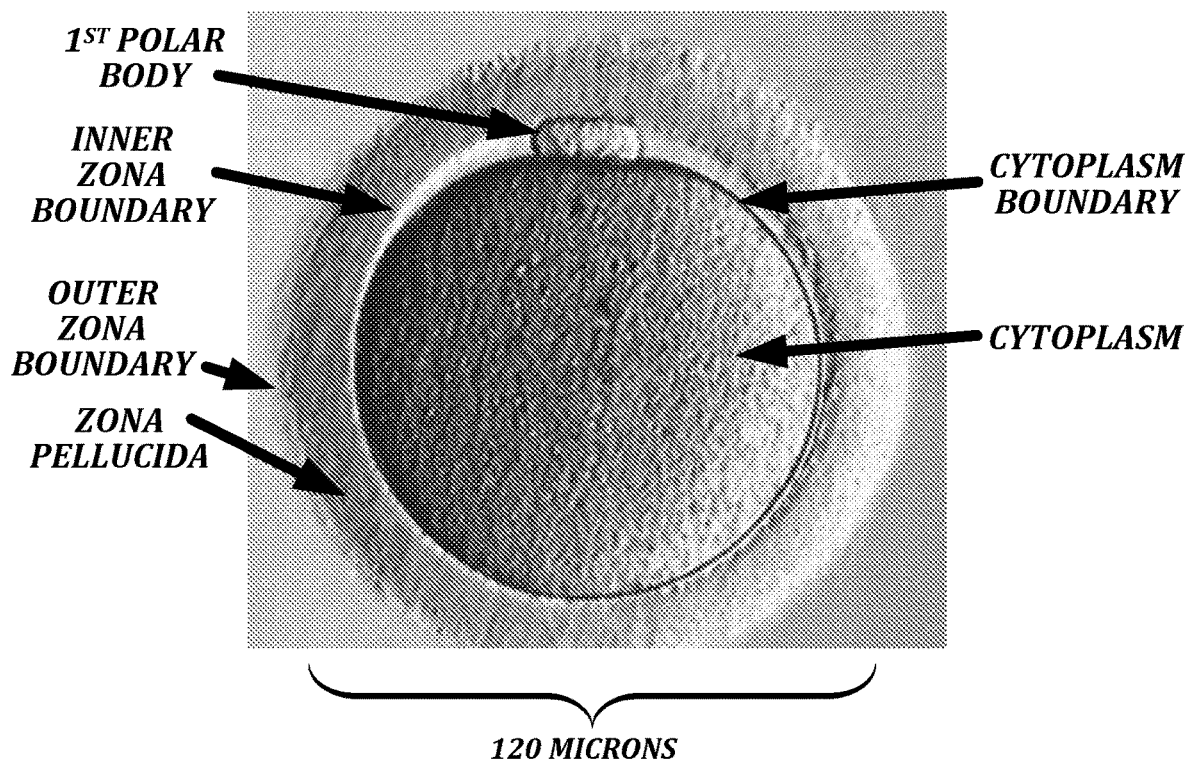
FIG. 1A is an image of a mature oocyte that may be analyzed by an automated image-based cell analysis system according to at least one embodiment of the present disclosure.

In the following description, numerous specific details are set forth in order to provide a thorough understanding of illustrative embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein. The illustrative examples provided herein are not intended to be exhaustive or to limit the claimed subject matter to the precise forms disclosed.

The present disclosure is directed to computerized image analysis, content-based image retrieval and cellular feature extraction of cells such as oocytes and pronuclear embryos, and their various intracellular components, and predicting outcomes related to cell quality, cell growth, or development (e.g., developmental changes that occur in comparison between oocytes and pronuclear embryos). The present disclosure includes an algorithm for the study of attributes of oocytes and pronuclear embryos that can be used in an automated analytic software tool to identify oocytes and pronuclear embryos with a high likelihood of implanting, among other possible outcomes related to reproductive potential. The present disclosure describes technology with unique clinical benefits distinct from anything commercially available. Disclosed embodiments are particularly significant in their ability to adapt to new cell science; as new outcomes are studied and linked to particular cell features, disclosed embodiments offer the ability to automatically extract those features from training images and associate with them with outcomes, generate decision models, and apply those decision models to new cell images in order to predict outcomes for the new cells.

Software systems for the interpretation of images are recent additions to the catalogue of programs with clinical application. Systems are now available for pattern and texture extraction in defined regions of interest. Extracted features can be added to catalogues to create archives of normal and abnormal images for comparisons and ultimately improved decision making and outcomes as well as possible cost reductions and improvements in work flow within labs. Video image analysis of embryos using dark field assessments has been described. No software, however, has been tested that evaluates attributes of oocytes or pronuclear embryos in standard bright field formats using the techniques described herein.

The present disclosure describes aspects of an automated analysis system that evaluates cells, such as oocytes and pronuclear embryos, in a new way while still being compatible with hardware systems using traditional bright field microscopy. Other computer image analysis systems use time-lapsed dark-field systems, and require separate monitoring hardware and additional personnel for maintenance and monitoring. In addition, data analyzing outcomes with such systems are of variable quality and have not consistently demonstrated any improvement in outcomes.

As suggested above, in contrast to existing systems, embodiments of the present disclosure have several potential marketplace advantages. As one possible advantage, existing hardware (e.g., in embryology labs) can be leveraged for additional benefit using embodiments of the present disclosure. For example, existing microscopy systems present in most labs may be used, with no additional hardware needed. As another possible advantage, existing image analysis software can be extended by incorporating embodiments of the present disclosure into an existing image analysis software system or into an integrated system of microscopy hardware an image analysis software.

The archive of images and outcomes also can be expanded to enhance precision and reliability of the algorithm. Image training can be performed on training images obtained from multiple sources (e.g., clinics, research institutions) stored in a common data repository. Using artificial intelligence, machine self-training can provide improvements over time thus leading to significant improvements in predicting outcomes with continued use. Embodiments described herein can be applied, for example, to both oocyte cryopreservation and embryo development to predict reproductive potential in oocytes prior to cryopreservation or after insemination during embryo development.

Further, embodiments described herein can provide useful analysis of a single cell, potentially offering greater ease in image acquisition and analysis, as well as improved clinical decision making as it relates to cell quality or development, e.g., prior to oocyte freezing for fertility preservation or oocyte donation and improved selection of which oocyte to inseminate and which pronuclear embryo to continue in culture. Embodiments described herein are useful in studying single cells, particularly in the context of reproductive medicine. After insemination and culturing, as the embryo expands in cell number (e.g., beyond 2 days of observation), the image field becomes more crowded, it becomes difficult to isolate individual cells, and the analytics become more complicated. As single cells, oocyte and pronuclear embryos provide excellent opportunities to extract information using computerized image analysis.

The present disclosure describes a quality model learned from existing images and related metadata, such as descriptions of outcomes related to cell quality, cell growth, and development. In the context of reproductive medicine, such outcomes include blastocyst formation, ploidy determinations, and clinical pregnancies. Reproductive potential can be assessed for, e.g., oocytes after freezing and pronuclear embryos. For example, as new forms of data become available and regulatory approvals are obtained for additional study (which may provide additional descriptions of outcomes, or new classes of outcomes), the dataset of existing images, metadata, and outcomes can be extended and the quality models can be improved.

The quality or reproductive potential of an oocyte or pronuclear embryo can be expressed in several different ways, such as the probability that the oocyte will fertilize when exposed to human sperm, the probability that the resulting embryo will reach a given stage of development (e.g., the blastocyst stage), or the probability that the embryo will result in a live birth when transferred to a uterus. In turn, probability can be expressed as a percentage chance, or as a high/medium/low chance, of reaching a given state of development. In some circumstances, there may also be some probability that genetic information (e.g., the genetic complement) or abnormal cell growth outcomes can be predicted, using techniques described in the present disclosure. For example, as new information becomes available linking genetic information or abnormal cell growth with cell features that can be identified in images using the image analysis techniques described herein, these techniques can correspondingly be used to deduce genetic information or abnormal cell growth outcomes from such images. In one possible scenario, instead of an outcome indicating whether an oocyte was successfully fertilized or how embryo development proceeded, an outcome may be whether abnormalities in chromosome number or genetic disorders are detected later on in development.

Additionally, aspects of the present disclosure provide the ability to gauge oocyte quality to guide decision making regarding oocyte cryopreservation. Oocyte preservation may be performed, for example, in an elective oocyte freezing program, in which it may be helpful to determine how many oocytes are to be frozen to maximize future fertility, or to determine a point of diminishing returns beyond which additional oocyte retrievals do not significantly increase the probability of future fertility. Thus, aspects of the present disclosure may be used to avoid performing too many or too few oocyte retrievals. Oocyte preservation also may be performed in an oocyte donation program, where the ability to prospectively assess oocyte potential will guide decision making about how many oocytes to batch for a given donation or whether to discard them and forego fertilization.

Aspects of the present disclosure improve on the current practice of using a single determination of whether an oocyte is mature or immature and freezing 6 to 8 oocytes per batch. Aspects of the present disclosure may be particularly useful in scenarios where the number of oocytes inseminated is limited, and the ability to identify an oocyte with the greatest reproductive potential becomes more important.

FIG. 1A is an image of a mature oocyte, with the zona pellucida (or "zona") and polar body indicated. In an illustrative embodiment, attributes of the cytoplasm, zona, and polar body can be automatically identified and analyzed, as described in detail below.

In an illustrative embodiment, the overall method is composed of two stages, each of which is composed of two phases. Stage one, the model construction stage, involves constructing a decision model (e.g., a model of quality for human oocytes or pronuclear embryos) from training images of cells (e.g., of oocytes or pronuclear embryos for which particular outcomes are known). Stage two, the employment stage, involves employing this model to predict outcomes for new cells being analyzed (e.g., in a clinical setting). For example, in the context of reproductive medicine, the employment stage may be used to determine the quality of an individual embryo.

Figure 2:
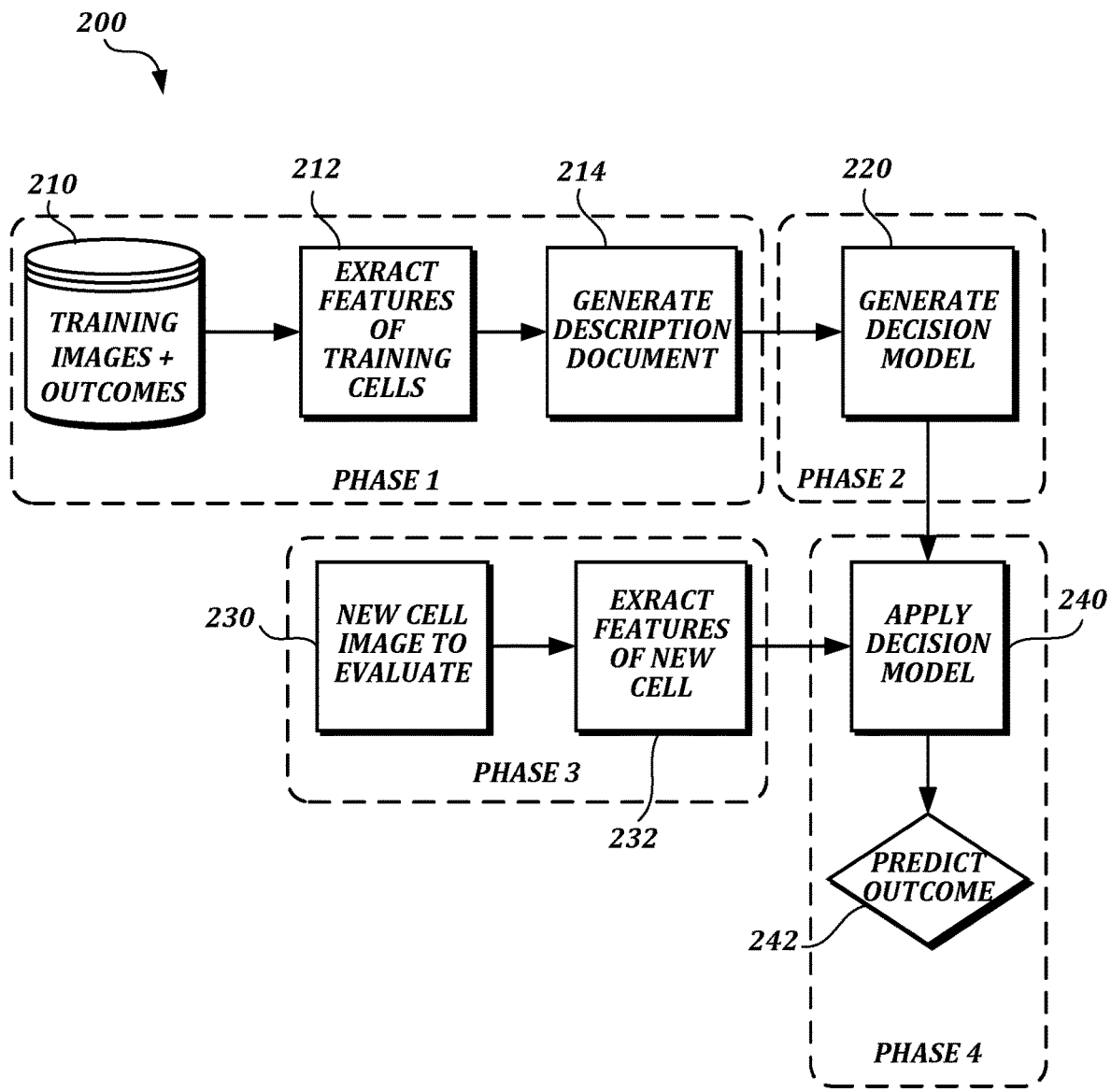
FIG. 2 is a flow diagram illustrating work flow in an automated image-based cell analysis system according to at least one embodiment of the present disclosure.

The method may be performed by an automated image-based cell analysis system, as described herein, implemented in a computer system comprising one or more computing devices. At a high level the automated image-based cell analysis system may include functionality for performing tasks described with reference to FIG. 2. The automated image-based cell analysis system may include multiple modules or engines to carry out different groups of tasks associated with different stages or phases, such as a model construction engine and a model employment engine, as described in detail below. Such modules or engines may be implemented in the same computing device, or in different computing devices. In turn, these sections or engines may include multiple submodules to carry out more specific tasks within the groups of tasks, such as particular types of feature extraction within the model construction engine.

Phase 1, the first phase of the model construction stage, is the feature extraction phase. In the example shown in FIG. 2, in phase 1 the automated image-based cell analysis system obtains a set of training images and related metadata from a data store 210 and converts them (e.g., using a model construction engine) into a description document. Like other digital images, the digital images that form the training set comprise pixels arranged in rows and columns. Each pixel is defined by a set of one or more sample values, with the number, meaning, and value range of the respective samples being determined by the format, color space, and bit depth (number of bits per channel) of the images. It will be understood that the techniques described herein can be adapted for analysis of digital images of various formats, resolutions, color spaces, bit depths, etc. For example, although some techniques are described herein as being performed on grayscale images at a predetermined resolution, various techniques for upscaling or downscaling image resolution, converting color images to grayscale, and the like, can be employed in combination with techniques described herein.

The feature extraction phase proceeds by extracting features 212 from the training images that describe the cells (e.g., oocytes or pronuclear embryos) in the images numerically, as described in detail below. In the context of reproductive medicine, this may include extraction of features such as the area measurement of the cytoplasm of each oocyte, or cytoplasmic or nuclear features of each pronuclear embryo in the training images. Although the features described herein focus on two-dimensional features such as two-dimensional boundaries, area within such boundaries, etc., it will be understood that such features may be extended to some three-dimensional features, such as volume, to the extent that such features can be accurately estimated based on information obtained from two-dimensional images.

The extracted features are then associated with outcomes in the description document 214. Further details of the features that can be included in a description document are provided below. (The term "document" is used herein to refer to a collection of the described information in any format suitable for further processing as described herein, and need not refer to a traditional document designed for human readability.) The data store may be updated as needed, e.g., to provide additional training images and related metadata.

In an illustrative embodiment, one required item in the description document is the description of one or more outcomes of what happened when the oocytes in the respective training images were fertilized. The outcomes associated with training images, also referred to herein as "Feature 1" of the respective training images, are not a function of the image data, but are metadata supplied along with the images. The metadata may include information related to developmental outcomes. With regard to a training image of an oocyte, for example, such metadata may include information about whether the oocyte fertilized and how embryo development proceeded.

Figure 3:
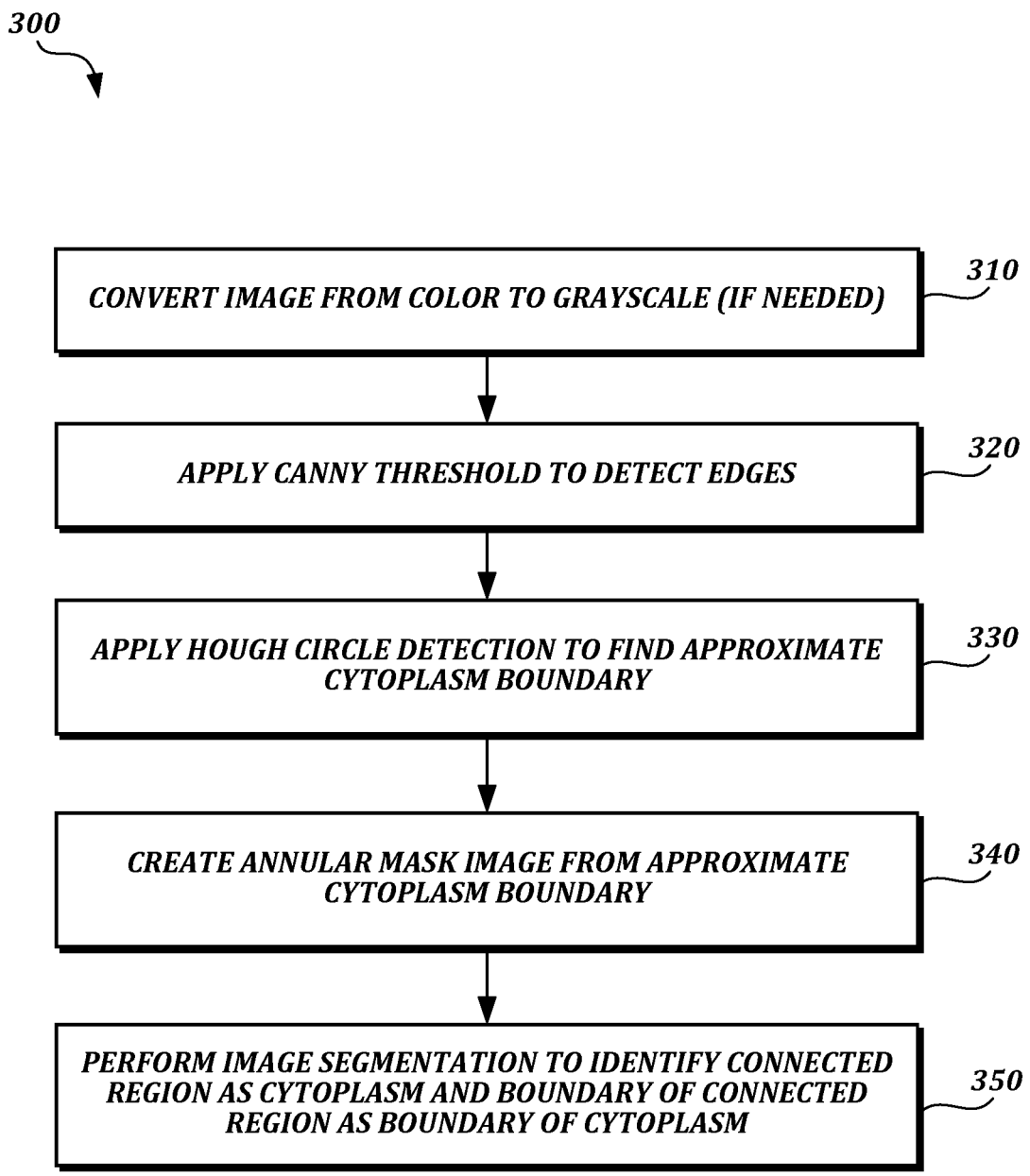
FIG. 3 is a flow diagram illustrating an algorithm for identification of a boundary of a cytoplasm using image analysis techniques according to at least one embodiment of the present disclosure.

In at least one embodiment, one or more of the following features 2-18 can be extracted from an oocyte image to create the description document in phase 1, as described below. It will be understood that extraction of some features described below (e.g., cytoplasm features) may be useful for many types of cells. For example, the pronuclear embryo is still a single cell (see FIG. 5), and its features also can be analyzed as described below:

2. Identification of the boundary of the cytoplasm, measured manually or with image analysis using an edge detection algorithm. An illustrative algorithm 300 is illustrated in FIG. 3:
    (a) At step 310, convert image from color to grayscale (if needed).
    (b) At step 320, apply an edge detection algorithm (e.g., Canny Threshold) to the grayscale image to detect edges.
    (c) At step 330, apply a circle detection algorithm (e.g., Hough Circle detection) to find an approximate cytoplasm boundary. In at least one embodiment, the circle detection algorithm may use known quantities of image resolution and magnification to control for size of circles to search from, and Gaussian blur on Canny-detected edges to further reduce number of detected circles, if needed, until only a single circle remains.
    If further processing steps that rely on the detected cytoplasm are to be performed, the following steps may be helpful:
    (d) At step 340, create an annular mask image from the circle, with inner and outer annulus radii as ratios of circle radius.
    (e) At step 350, perform image segmentation on the original source image to identify a connected region as the cytoplasm. For example, a GrabCut method can be used, with the resulting connected region being the cytoplasm, and the boundary of the connected region being the boundary of the cytoplasm. The annular mask can be used to restrict the search. A mask image may be created containing only pixels from the connected region. This image simplifies computing further cytoplasm features.

Figure 4:
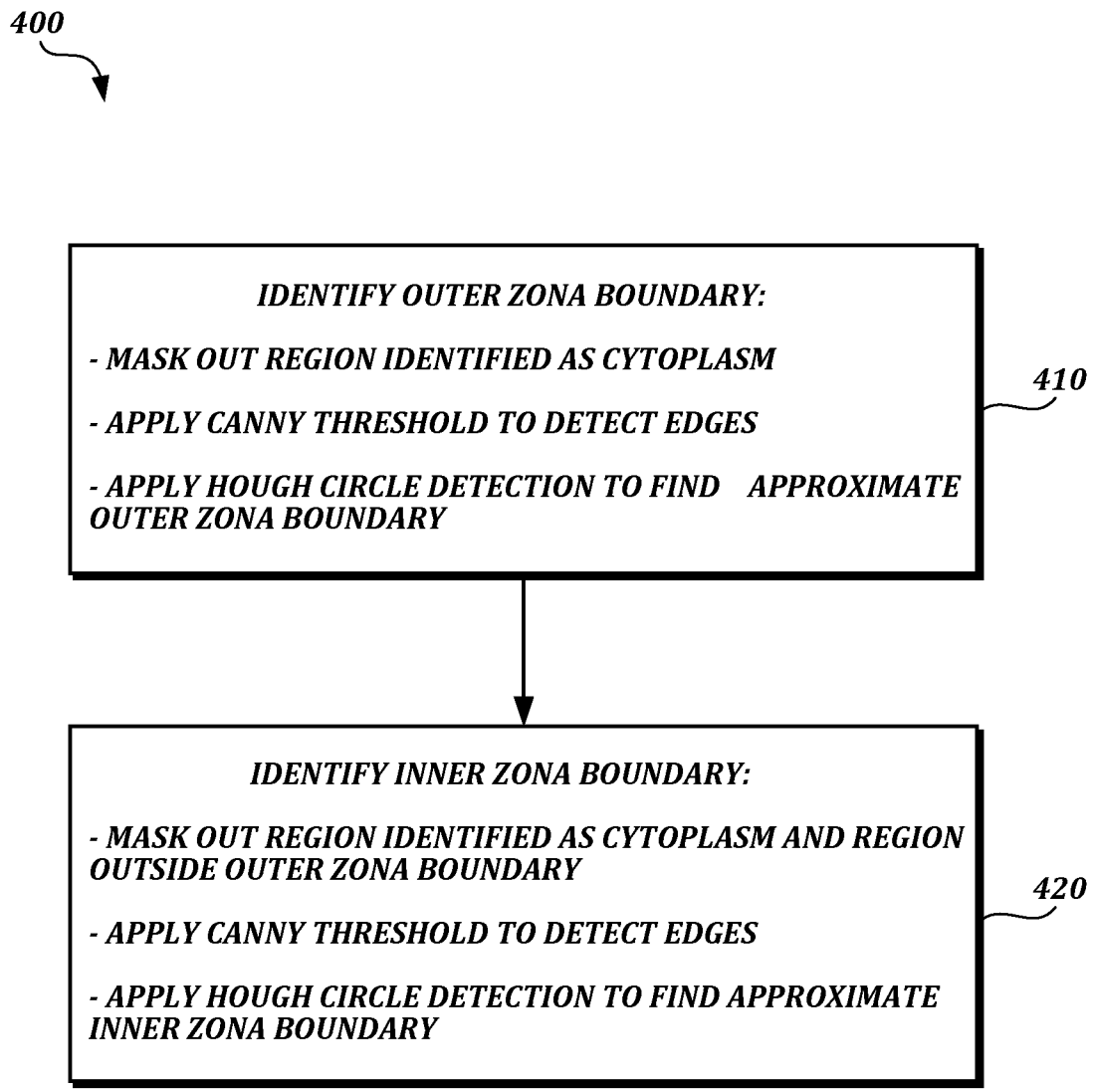
FIG. 4 is a flow diagram illustrating an algorithm for identification of inner and outer edges of a zona pellucida of an oocyte or pronuclear embryo according to at least one embodiment of the present disclosure.

3. Total area of the cytoplasm in the image, defined by the portion of the image inside the boundary identified in feature 2. (The volume of the cytoplasm can also be estimated based on this information.)
4. Aspect ratio of the cytoplasm, being the ratio of the shortest distance across the cytoplasm to the longest.
5. Convexity of the cytoplasm boundary. This feature may relate to comparative changes in the cytoplasm transitioning from oocyte to pronuclear embryo. As an example, convexity may be calculated as follows:
    (a) Compute the convex hull of the mask image generated in feature 2, step (e), above.
    (b) Calculate the ratio of the area of the mask and area of the convex hull.
6. Average image intensity of the cytoplasm. For example, average intensity may be calculated by averaging the corresponding pixel values of the identified cytoplasm in a grayscale image (in which the value of each pixel is a single sample), or by averaging a particular value for corresponding pixels (such as brightness) when represented in a color space such as HSB (Hue-Saturation-Brightness).
7. Standard deviation of the image intensity of the cytoplasm.
8. Smoothness of the cytoplasm, measured by applying a Gaussian filter to the cytoplasm image, varying the size of the Gaussian filter and recording how that affects the number of features that can be detected in the cytoplasm by, e.g., Canny edge detector, Harris corner detector, or another process which detects features which vary by image smoothness. As the Gaussian smoothing is increased the number of features decreases until no features are detected. The system can track how fast the number of features decreases and how much smoothing is needed to eliminate features entirely, which provides information about the smoothness of the cytoplasm.
9. Subsampled examination of the cytoplasm, where the cytoplasm area is divided by a grid, and each of the grid areas is subjected to techniques 6, 7 and 8. The results of these procedures can be characterized by:
    a. variation of the outcomes for the individual grid areas, or
    b. counts generated when given thresholds are exceeded for a grid area.
10. Identification of the boundary of the polar body, measured manually or with image analysis using an edge detection algorithm.
11. Indication based on feature 10, above, as to whether the polar body exists for the oocyte or pronuclear embryo.
12. For the polar body, features analogous to features 3-9, above.
13. Identification of the inner and outer edges of the zona pellucida of the oocyte or pronuclear embryo. The inner boundary may be coincident with the boundary of the cytoplasm, or gaps may exist between them (perivitelline space). An illustrative algorithm 400 is illustrated in FIG. 4:
    (a) At step 410, to identify the outer zona boundary, mask out the region of the image that has been identified as containing the boundary of the cytoplasm in feature 2, above.
    (b) At step 420, to identify the inner zona boundary, mask out parts of the image inside the cytoplasm and outside the outer zona boundary, and then identify the inner zona boundary by applying edge detection and circle detection algorithms as in feature 2.

In addition, image sharpening can be performed before the edge detection steps so that the zona edges are more readily apparent.

14. For the zona pellucida, features analogous to features 3-9, above.
15. A measurement of the smoothness of the boundaries of the zona, describing the size and number of features found on the edges.
16. Alignment of the principal axes of the cytoplasm and the zona. For example, the system may calculate axes by finding a minimal bounding rectangle around the mask of the cytoplasm and the zona, with alignment of the sides of the rectangle defining the principal axes. As another example, the system may determine alignment by estimating the oocyte perimeter from an interior reference point (e.g., centroid) and iteratively region-growing no further than the oocyte edge, passing coordinates through this centroid along its major and minor axes to the oocyte edge, and measuring coordinate lengths within the estimated oocyte region.
17. Area of the perivitelline space between the cytoplasm and the zona. This is the area within the inner zona which is not also within the cytoplasm.
18. For the perivitelline space, features analogous to features 3-9, above.

An illustrative description document for 6 images with outcomes and 5 features associated with those images is shown in Table 1, below.

Figure 1B:
FIG. 1B is an image of abnormal oocytes that may be analyzed by an automated image-based cell analysis system according to at least one embodiment of the present disclosure.

The features described herein may be used to detect abnormalities in, for example, texture, inclusion bodies, and shape or size, such as the abnormalities depicted in the oocytes shown in FIG. 1B.

In addition to the image analysis tools described above, other tools, such as colorization and color filters, also may be used for feature extraction. For example, to the extent that a particular color filter is useful for detecting a particular feature, the color filter can be applied to a color image of the cell before proceeding with further analysis of the image. This process may be performed, for example, on a color source image prior to conversion of the color source image to grayscale for detection of other features.

As noted above, it is not required for all of the features described above to be extracted in every case, or for all features to be extracted automatically. In some cases, automatic analysis can be performed on manually measured features (e.g., features measured with the help of a customized graphical user interface) or on combinations of manually measured features and automatically extracted features.

Referring again to FIG. 2, the second phase of the model construction stage (phase 2), is the learning or training phase. Phase 2 determines which features extracted in phase 1 materially affect predictive ability in phase 4. Features selected for inclusion in the decision model may include, for example, features having a numerical predictive value that exceeds a threshold value. Features not selected for inclusion in the decision model, which do not have significant predictive value, can be excluded in phases 3 and 4, which are described in detail below. In phase 2, the model con-

TABLE 1

Illustrative description document

| Image | Outcome | Cytoplasm size ratio | Intensity mean | Intensity std dev | Canny 1.000000 | Harris 13.000000 |
|---|---|---|---|---|---|---|
| 1 | 1 | 0.126841 | 0.478617 | 0.0623425 | 0.187357 | 0.0688431 |
| 2 | 0 | 0.108994 | 0.465757 | 0.0623978 | 0.198311 | 0.0519201 |
| 3 | 0 | 0.117361 | 0.455848 | 0.0678655 | 0.197325 | 0.0439613 |
| 4 | 1 | 0.0966727 | 0.514367 | 0.0622328 | 0.0312051 | 0.00810862 |
| 5 | 1 | 0.108249 | 0.513011 | 0.0877929 | 0.164327 | 0.0360605 |
| 6 | 0 | 0.117361 | 0.472042 | 0.0797936 | 0.179902 | 0.0625631 |

Other features that may be extracted with image analysis techniques include cytoplasmic texture features, texture distribution, densities, and clustering.

Figure 5:
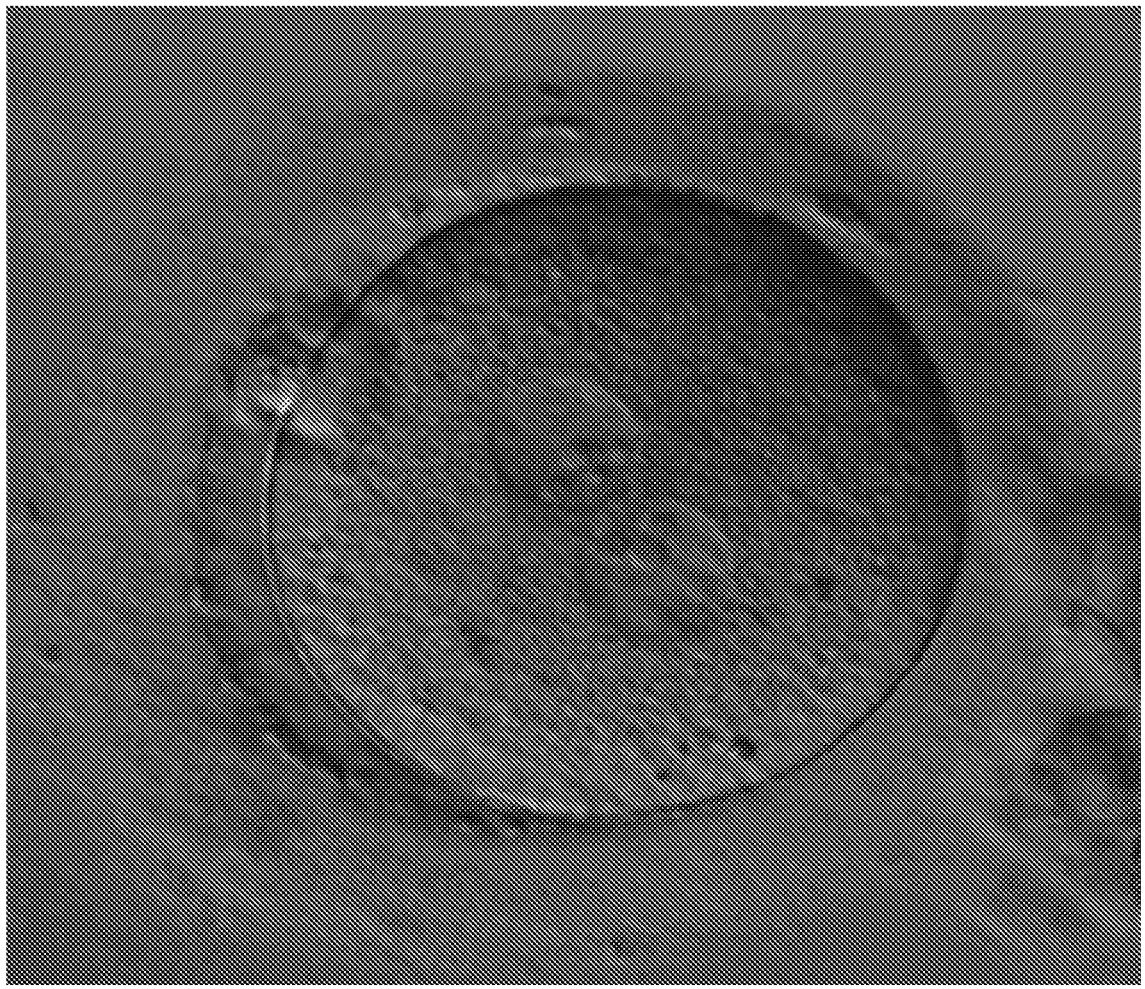
FIG. 5 is an image of a pronuclear embryo that may be analyzed by an automated image-based cell analysis system according to at least one embodiment of the present disclosure.

An illustrative image of a pronuclear embryo is shown in FIG. 5. For pronuclear embryos, in addition to the applicable features described above, any of the additional features 19-23 described below can be extracted for the pronuclei in the center of the cytoplasm, as follows:

19. Identification of the boundaries of the pronuclei, measured manually or with image analysis using an edge detection algorithm.
20. The area or volume of the pronuclei, measured individually and relative to each other.
21. The aspect ratio of the pronuclei measured individually and relative to each other.
22. For the pronuclei, features analogous to features 5-9, above, and comparisons of those features between the two pronuclei.
23. For each of the features that are common to pronuclei and oocyte analysis, generate a set of comparison features by subtraction or division.

struction engine consumes or reads (e.g., using the model construction engine) the descriptions (e.g., numeric descriptions) in the description document and computes a mathematical optimization to determine which of the features are significant in determining quality of outcomes. Thus, the output of phase 1 is the input for phase 2. The output of phase 2 is a model (see "generate decision model" block 220 shown in FIG. 2) that can be used to predict outcomes. For example, in the field of reproductive medicine, such predicted outcomes may be used to determine quality or reproductive potential given the numeric features for a given oocyte or pronuclear embryo. This can be referred to as constructing a model with labeled training data. In at least one embodiment, the image analysis and attributes that the software detects are correlated with outcome and weighted according to significance.

In at least one embodiment, a portion of the training data is held out to use for validating the model, and training is done on the remaining training data using cross-validation to ensure the stability of the model. The model can be constructed using logistic regression, decision trees, or some other method that consumes labeled training data. Sufficient training data is required to achieve a significant result from training. When cross-validation implies that the model is predictive, the held-out portion of the training data is used to validate model quality. Training in phase 2 also may be performed using unsupervised learning such as k-means or neural networks to segment the training data into classes. After classes have been identified, the predominant label from the samples in each class is assigned to each class. The learning phase also may be performed using other machine learning methods.

As noted above, the output of phase 2 is a decision model which can be used to predict outcomes, such as cell quality or reproductive potential. As further noted above, the quality or reproductive potential of an oocyte or pronuclear embryo can be expressed in several different ways, such as the probability that the embryo will be chromosomally normal or euploid, or abnormal or aneuploid, the probability that the oocyte will fertilize when exposed to human sperm, the probability that the resulting embryo will reach a given stage of development (e.g., the blastocyst stage), or the probability the embryo will result in a live birth when transferred to a uterus. In turn, probability can be expressed as a percentage chance, or as a high/medium/low chance, of reaching a given state of development.

In phase 3, the first phase of the employment stage, the automated image-based cell analysis system performs (e.g., using the model employment engine) feature extraction on a new image 230 (e.g., an image of a single oocyte or pronuclear embryo). In this phase, the automated image-based cell analysis system generates features 232 for the new image corresponding to one or more features that were generated for the training images in phase 1, other than feature 1 (outcome), which is not yet known. It is not necessary for all of the features described in phase 1 to be extracted for new images in phase 3. For example, features that have been determined in phase 2 not to have predictive value need not be extracted in phase 3.

Although automatic feature extraction has many benefits, as described herein, it is also possible to use the techniques described herein on one or more manually extracted features. For accurate modeling, features that are extracted manually in phase 1 can also be extracted manually in phase 3.

To ensure that values for the features described herein can be compared between images, for both learning and employment phases, a rule that all images be of the same resolution and magnification can be enforced. To comply with this rule, the original images do not necessarily need to be of the same resolution and magnification. Instead, images can be scaled and cropped as needed, either manually or automatically.

In phase 4, the automated image-based cell analysis system predicts (e.g., using the model employment engine) one or more outcomes 242 for the cell (e.g., oocyte or pronuclear embryo) in the new image by applying the decision model 240 generated in phase 2 to the features extracted in phase 3. For example, a score between 0 and 1 can be assigned, with a greater score indicating a better predicted outcome. The predicted outcome adds a significant benefit compared to, for example, older methods of selecting oocytes for insemination based solely on maturity. A threshold score can be set, below which the oocyte regardless of maturity may be discarded as unlikely if not impossible to yield a blastocyst and live birth. Depending on the design of the decision model, the features may be weighted together in some combination, or used as decision points in a decision tree application to determine the likely outcomes for the cell (e.g., oocyte or pronuclear embryo) for one or more of the scenarios provided as outcomes in feature 1 of the training set.

Cells can be analyzed separately, or in combination. For example, the quality of oocytes and pronuclear embryos can be analyzed individually and then combined to form an overall quality score.

As described above, although many features may be extracted, some subsets may be more predictive than others. The system can use various types of predictive analytics to determine which features or combinations of features are more predictive. In an illustrative embodiment, an automated image-based cell analysis system identifies 5 cellular attributes of oocytes. These attributes were selected as possibly predictive of the likelihood reproductive potential of the oocyte and of blastocyst formation and implantation. A numerical score between 0.0 (lowest) and 1.0 (highest) was calculated to estimate these likelihoods. In this illustrative embodiment, the algorithm employs Stochastic Gradient Descent implemented in the Python programming language through the SciPy extension. Feature extraction uses a variety of additional techniques in C++, including a Hough Circle detector and a Harris Corner detector. Main outcome measurements include calculation of an Oocyte Score (OS) to identify oocytes with a high reproductive potential and likelihood of blastocyst formation and to compare the OS (Group 1) to selection using standard morphology (Group 2) and to a computerized video monitoring system (Group 3).

In at least one embodiment, an automated image-based cell analysis system can receive software updates over a network, to provide updates to the analysis system, the training data, or other data.

Illustrative Devices and Operating Environments

Unless otherwise specified in the context of specific examples, described techniques and tools may be implemented by any suitable computing device or set of devices.

In any of the described examples, an engine (e.g., a software engine working in combination with computer hardware and microscopy systems) may be used to perform actions described herein. An engine includes logic (e.g., in the form of computer program code) configured to cause one or more computing devices to perform actions described herein as being associated with the engine. For example, a computing device can be specifically programmed to perform the actions by having installed therein a tangible computer-readable medium having computer-executable instructions stored thereon that, when executed by one or more processors of the computing device, cause the computing device to perform the actions. The particular engines described herein are included for ease of discussion, but many alternatives are possible. For example, actions described herein as associated with two or more engines on multiple devices may be performed by a single engine. As another example, actions described herein as associated with a single engine may be performed by two or more engines on the same device or on multiple devices.

In any of the described examples, a data store contains data as described herein and may be hosted, for example, by a database management system (DBMS) to allow a high level of data throughput between the data store and other components of a described system. The DBMS may also allow the data store to be reliably backed up and to maintain a high level of availability. For example, a data store may be accessed by other system components via a network, such as a private network in the vicinity of the system, a secured transmission channel over the public Internet, a combination of private and public networks, and the like. Instead of or in addition to a DBMS, a data store may include structured data stored as files in a traditional file system. Data stores may reside on computing devices that are part of or separate from components of systems described herein. Separate data stores may be combined into a single data store, or a single data store may be split into two or more separate data stores.

Some of the functionality described herein may be implemented in the context of a client-server relationship. In this context, server devices may include suitable computing devices configured to provide information and/or services described herein. Server devices may include any suitable computing devices, such as dedicated server devices. Server functionality provided by server devices may, in some cases, be provided by software (e.g., virtualized computing instances or application objects) executing on a computing device that is not a dedicated server device. The term "client" can be used to refer to a computing device that obtains information and/or accesses services provided by a server over a communication link. However, the designation of a particular device as a client device does not necessarily require the presence of a server. At various times, a single device may act as a server, a client, or both a server and a client, depending on context and configuration. Actual physical locations of clients and servers are not necessarily important, but the locations can be described as "local" for a client and "remote" for a server to illustrate a common usage scenario in which a client is receiving information provided by a server at a remote location. Alternatively, a peer-to-peer arrangement, or other models, can be used.

Figure 6:
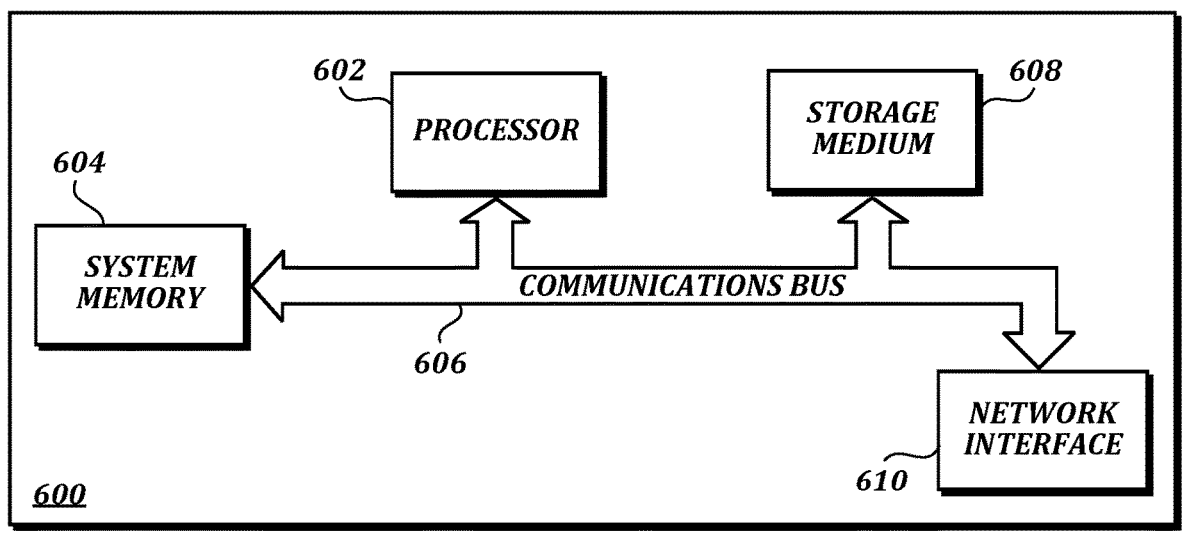
FIG. 6 is a block diagram that illustrates aspects of an illustrative computing device appropriate for use in accordance with embodiments of the present disclosure.

FIG. 6 is a block diagram that illustrates aspects of an illustrative computing device 600 appropriate for use in accordance with embodiments of the present disclosure. The description below is applicable to servers, personal computers, mobile phones, smart phones, tablet computers, embedded computing devices, and other currently available or yet-to-be-developed devices that may be used in accordance with embodiments of the present disclosure. Computing devices described herein may be integrated with specialized hardware, such as microscopy systems, for obtaining images, or as stand-alone devices that obtain images for analysis in some other way, such as by receiving images stored remotely in a cloud computing arrangement.

In its most basic configuration, the computing device 600 includes at least one processor 602 and a system memory 604 connected by a communication bus 606. Depending on the exact configuration and type of device, the system memory 604 may be volatile or nonvolatile memory, such as read only memory ("ROM"), random access memory ("RAM"), EEPROM, flash memory, or other memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 6, the computing device 600 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols, such as WiFi, 2G, 3G, 4G, LTE, WiMAX, Bluetooth, and/or the like.

In the illustrative embodiment depicted in FIG. 6, the computing device 600 also includes a storage medium 608. However, services may be accessed using a computing device that does not include means for persisting data to a local storage medium. Therefore, the storage medium 608 depicted in FIG. 6 is optional. In any event, the storage medium 608 may be volatile or nonvolatile, removable or nonremovable, implemented using any technology capable of storing information such as, but not limited to, a hard drive, solid state drive, CD-ROM, DVD, or other disk storage, magnetic tape, magnetic disk storage, and/or the like.

As used herein, the term "computer-readable medium" includes volatile and nonvolatile and removable and nonremovable media implemented in any method or technology capable of storing information, such as computer-readable instructions, data structures, program modules, or other data. In this regard, the system memory 604 and storage medium 608 depicted in FIG. 6 are examples of computer-readable media.

For ease of illustration and because it is not important for an understanding of the claimed subject matter, FIG. 6 does not show some of the typical components of many computing devices. In this regard, the computing device 600 may include input devices, such as a keyboard, keypad, mouse, trackball, microphone, video camera, touchpad, touchscreen, electronic pen, stylus, and/or the like. Such input devices may be coupled to the computing device 600 by wired or wireless connections including RF, infrared, serial, parallel, Bluetooth, USB, or other suitable connection protocols using wireless or physical connections.

In any of the described examples, input data can be captured by input devices and processed, transmitted, or stored (e.g., for future processing). The processing may include encoding data streams, which can be subsequently decoded for presentation by output devices. Media data can be captured by multimedia input devices and stored by saving media data streams as files on a computer-readable storage medium (e.g., in memory or persistent storage on a client device, server, administrator device, or some other device). Input devices can be separate from and communicatively coupled to computing device 600 (e.g., a client device), or can be integral components of the computing device 600. In some embodiments, multiple input devices may be combined into a single, multifunction input device (e.g., a video camera with an integrated microphone). The computing device 600 may also include output devices such as a display, speakers, printer, etc. The output devices may include video output devices such as a display or touchscreen. The output devices also may include audio output devices such as external speakers or earphones. The output devices can be separate from and communicatively coupled to the computing device 600, or can be integral components of the computing device 600. Input functionality and output functionality may be integrated into the same input/output device (e.g., a touchscreen). Any suitable input device, output device, or combined input/output device either currently known or developed in the future may be used with described systems.

In general, functionality of computing devices described herein may be implemented in computing logic embodied in hardware or software instructions, which can be written in a programming language, such as C, C++, COBOL, JAVA™, PHP, Perl, Python, Ruby, HTML, CSS, JavaScript, VBScript, ASPX, Microsoft .NET™ languages such as C #, and/or the like. Computing logic may be compiled into executable programs or written in interpreted programming languages. Generally, functionality described herein can be implemented as logic modules that can be duplicated to provide greater processing capability, merged with other modules, or divided into sub-modules. The computing logic can be stored in any type of computer-readable medium (e.g., a non-transitory medium such as a memory or storage medium) or computer storage device and be stored on and executed by one or more general-purpose or special-purpose processors, thus creating a special-purpose computing device configured to provide functionality described herein.

Extensions and Alternatives

Many alternatives to the systems and devices described herein are possible. For example, individual modules or subsystems can be separated into additional modules or subsystems or combined into fewer modules or subsystems. As another example, modules or subsystems can be omitted or supplemented with other modules or subsystems. As another example, functions that are indicated as being performed by a particular device, module, or subsystem may instead be performed by one or more other devices, modules, or subsystems. Although some examples in the present disclosure include descriptions of devices comprising specific hardware components in specific arrangements, techniques and tools described herein can be modified to accommodate different hardware components, combinations, or arrangements. Further, although some examples in the present disclosure include descriptions of specific usage scenarios, techniques and tools described herein can be modified to accommodate different usage scenarios. Functionality that is described as being implemented in software can instead be implemented in hardware, or vice versa.

Many alternatives to the techniques described herein are possible. For example, processing stages in the various techniques can be separated into additional stages or combined into fewer stages. As another example, processing stages in the various techniques can be omitted or supplemented with other techniques or processing stages. As another example, processing stages that are described as occurring in a particular order can instead occur in a different order. As another example, processing stages that are described as being performed in a series of steps may instead be handled in a parallel fashion, with multiple modules or software processes concurrently handling one or more of the illustrated processing stages. As another example, processing stages that are indicated as being performed by a particular device or module may instead be performed by one or more other devices or modules.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the claimed subject matter.

The embodiments of the invention in which an exclusive property or privilege is claimed are defined as follows:

1. A computer-implemented method comprising:
   automatically converting a set of training images of cells and related outcome metadata into a description document by extracting features from the training images that describe the cells and associating the extracted features with the outcome metadata, wherein the training images are obtained using bright-field microscopy;
   based on the description document, automatically computing a decision model that can be used to predict outcomes of new cells,
   wherein the cells are oocytes or pronuclear embryos, and
   wherein the extracted features include one or more of the following:
      a boundary of a polar body, measured manually or with image analysis using an edge detection algorithm;
      an indication as to whether the polar body exists;
      identification of inner and outer edges of a zona pellucida;
      identification of perivitelline space;
      a measurement of smoothness of the edges of the zona pellucida;
      alignment of principal axes of the cytoplasm and the zona;
      total area of the polar body, the zona pellucida, or the perivitelline space;
      aspect ratio of the polar body, the zona pellucida, or the perivitelline space;
      convexity of a boundary of the polar body, the zona pellucida, or the perivitelline space;
      average image intensity of the polar body, the zona pellucida, or the perivitelline space;
      standard deviation of the image intensity of the polar body, the zona pellucida, or the perivitelline space;
      smoothness of the polar body, the zona pellucida, or the perivitelline space; and
      subsampled image intensity or smoothness for grid areas within the polar body, the zona pellucida, or the perivitelline space.

2. The method of claim 1, wherein the one or more outcomes include one or more of the following:
   quality or reproductive potential of a new oocyte,
   whether abnormalities in chromosome number are detected later in development,
   whether genetic disorders are detected later in development, and
   abnormal cell growth outcomes.

3. The method of claim 2, wherein the quality or reproductive potential of the new oocyte is expressed as one or more of: a probability that the oocyte will fertilize when exposed to human sperm, a probability that a resulting embryo will reach a given stage of development, or a probability that the resulting embryo will result in a live birth when transferred to a uterus.

4. The method of claim 1 further comprising:
   automatically extracting features from images that describe new cells, wherein the images that describe the new cells are obtained using bright-field microscopy;
   predicting one or more outcomes for the new cells by applying the decision model to the features extracted from the images that describe the new cells.

5. The method of claim 4, wherein the features extracted from the images that describe new cells correspond to features selected for inclusion in the decision model.

6. The method of claim 4, wherein the one or more outcomes include one or more of quality or reproductive potential for a new oocyte, whether abnormalities in chromosome number are detected later in development, whether genetic disorders are detected later in development, and abnormal cell growth outcomes.

7. The method of claim 6, wherein the quality or reproductive potential of the new oocyte is expressed as one or more of: a probability that the oocyte will fertilize when exposed to human sperm, a probability that a resulting embryo will reach a given stage of development, or a probability that the resulting embryo will result in a live birth when transferred to a uterus.

8. A computer-implemented method comprising:
automatically converting a set of training images of cells and related outcome metadata into a description document by extracting features from the training images that describe the cells and associating the extracted features with the outcome metadata, wherein the training images are obtained using bright-field microscopy;
based on the description document, automatically computing a decision model that can be used to predict outcomes of new cells,
wherein the cells are oocytes or pronuclear embryos, and
wherein the extracted features include one or more of the following for a pronuclear embryo comprising pronuclei:
identification of the boundaries of the pronuclei, measured manually or with image analysis using an edge detection algorithm;
area of the pronuclei, measured individually and/or relative to each other;
aspect ratio of the pronuclei, measured individually and/or relative to each other;
convexity of a boundary of one or more of the pronuclei;
average image intensity of one or more of the pronuclei;
standard deviation of the image intensity of one or more of the pronuclei;
smoothness of one or more of the pronuclei; and
subsampled image intensity or smoothness for grid areas within one or more of the pronuclei.

9. The method of claim 8, wherein the one or more outcomes include one or more of the following:
whether abnormalities in chromosome number are detected later in development,
whether genetic disorders are detected later in development, and
abnormal cell growth outcomes.

10. The method of claim 8 further comprising:
automatically extracting features from images that describe new cells, wherein the images that describe the new cells are obtained using bright-field microscopy;
predicting one or more outcomes for the new cells by applying the decision model to the features extracted from the images that describe the new cells.

11. The method of claim 10, wherein the features extracted from the images that describe new cells correspond to features selected for inclusion in the decision model.

12. A computer-implemented method comprising:
automatically extracting features that describe new cells from new cell images; and
predicting one or more outcomes for the new cells by applying a decision model to the features extracted from the new cell images, wherein the decision model is based on a description document that associates outcome metadata with features extracted from training images, wherein the training images and the new cell images are obtained using bright-field microscopy,
wherein the new cells are oocytes or pronuclear embryos, and
wherein the features extracted from the new cell images and the features extracted from the training images include one or more of the following:
a boundary of a polar body, measured manually or with image analysis using an edge detection algorithm;
an indication as to whether the polar body exists;
identification of inner and outer edges of a zona pellucida;
identification of perivitelline space;
a measurement of smoothness of the edges of the zona pellucida;
alignment of principal axes of the cytoplasm and the zona;
total area of the polar body, the zona pellucida, or the perivitelline space;
aspect ratio of the polar body, the zona pellucida, or the perivitelline space;
convexity of the boundary of the polar body, the zona pellucida, or the perivitelline space;
average image intensity of the polar body, the zona pellucida, or the perivitelline space;
standard deviation of the image intensity of the polar body, the zona pellucida, or the perivitelline space;
smoothness of the polar body, the zona pellucida, or the perivitelline space; and
subsampled image intensity or smoothness for grid areas within the polar body, the zona pellucida, or the perivitelline space.

13. The method of claim 12, wherein the one or more outcomes include one or more of the following:
quality or reproductive potential of a new oocyte,
whether abnormalities in chromosome number are detected later in development,
whether genetic disorders are detected later in development, and
abnormal cell growth outcomes.

14. The method of claim 13, wherein the quality or reproductive potential of the new oocyte is expressed as one or more of: a probability that the oocyte will fertilize when exposed to human sperm, a probability that a resulting embryo will reach a given stage of development, or a probability that the resulting embryo will result in a live birth when transferred to a uterus.

15. A computer-implemented method comprising:
automatically extracting features that describe new cells from new cell images; and
predicting one or more outcomes for the new cells by applying a decision model to the features extracted from the new cell images, wherein the decision model is based on a description document that associates outcome metadata with features extracted from training images, wherein the training images and the new cell images are obtained using bright-field microscopy, wherein the new cells are oocytes or pronuclear embryos, and wherein the features extracted from the new cell images and the features extracted from the training images include one or more of the following for a pronuclear embryo comprising pronuclei:
identification of the boundaries of the pronuclei, measured manually or with image analysis using an edge detection algorithm;
area of the pronuclei, measured individually and/or relative to each other;
aspect ratio of the pronuclei, measured individually and/or relative to each other;
convexity of a boundary of one or more of the pronuclei;
average image intensity of one or more of the pronuclei;
standard deviation of the image intensity of one or more of the pronuclei;
smoothness of one or more of the pronuclei; and
subsampled image intensity or smoothness for grid areas within one or more of the pronuclei.

16. The method of claim 15, wherein the one or more outcomes include one or more of the following:

whether abnormalities in chromosome number are detected later in development,
whether genetic disorders are detected later in development, and
abnormal cell growth outcomes.

17. A computer-implemented method comprising:
automatically extracting features that describe new cells from new cell images; and
predicting one or more outcomes for the new cells by applying a decision model to the features extracted from the new cell images, wherein the decision model is based on a description document that associates outcome metadata with features extracted from training images, wherein the training images and the new cell images are obtained using bright-field microscopy, wherein the new cells are oocytes or pronuclear embryos, and wherein the one or more outcomes include one or more of the following:
quality or reproductive potential for a new oocyte,
whether abnormalities in chromosome number are detected later in development,
whether genetic disorders are detected later in development, and
abnormal cell growth outcomes.

18. The method of claim 17, wherein the quality or reproductive potential of the new oocyte is expressed as one or more of: a probability that the oocyte will fertilize when exposed to human sperm, a probability that a resulting embryo will reach a given stage of development, or a probability that the resulting embryo will result in a live birth when transferred to a uterus.

19. A non-transitory computer-readable medium having stored thereon computer-executable instructions configured to cause one or more computing devices to perform steps comprising:
automatically extracting features that describe new cells from new cell images; and
predicting one or more outcomes for the new cells by applying a decision model to the features extracted from the new cell images, wherein the decision model is based on a description document that associates outcome metadata with features extracted from training images, wherein the training images and the new cell images are obtained using bright-field microscopy, wherein the new cells are oocytes or pronuclear embryos, and wherein the one or more outcomes include one or more of the following:
quality or reproductive potential of a new oocyte,
whether abnormalities in chromosome number are detected later in development,
whether genetic disorders are detected later in development, and
abnormal cell growth outcomes.

20. The computer-readable medium of claim 19, wherein the features extracted from the new cell images and the features extracted from the training images include one or more of the following:
a boundary of a polar body, measured manually or with image analysis using an edge detection algorithm;
an indication as to whether the polar body exists;
identification of inner and outer edges of a zona pellucida;
identification of perivitelline space;
a measurement of smoothness of the edges of the zona pellucida;
alignment of principal axes of the cytoplasm and the zona;
total area of the polar body, the zona pellucida, or the perivitelline space;
aspect ratio of the polar body, the zona pellucida, or the perivitelline space;
convexity of the boundary of the polar body, the zona pellucida, or the perivitelline space;
average image intensity of the polar body, the zona pellucida, or the perivitelline space;
standard deviation of the image intensity of the polar body, the zona pellucida, or the perivitelline space;
smoothness of the polar body, the zona pellucida, or the perivitelline space; and
subsampled image intensity or smoothness for grid areas within the polar body, the zona pellucida, or the perivitelline space.

21. The computer-readable medium of claim 19, wherein the features extracted from the new cell images and the features extracted from the training images include one or more of the following for a pronuclear embryo comprising pronuclei:
identification of the boundaries of the pronuclei, measured manually or with image analysis using an edge detection algorithm;
area of the pronuclei, measured individually and/or relative to each other;
aspect ratio of the pronuclei, measured individually and/or relative to each other;
convexity of a boundary of one or more of the pronuclei;
average image intensity of one or more of the pronuclei;
standard deviation of the image intensity of one or more of the pronuclei;
smoothness of one or more of the pronuclei; and
subsampled image intensity or smoothness for grid areas within one or more of the pronuclei.

22. The computer-readable medium of claim 19, wherein the quality or reproductive potential of the new oocyte is expressed as one or more of: a probability that the oocyte will fertilize when exposed to human sperm, a probability that a resulting embryo will reach a given stage of development, or a probability that the resulting embryo will result in a live birth when transferred to a uterus.

23. A system comprising one or more computing devices programmed to perform steps comprising:
automatically extracting features that describe new cells from new cell images; and
predicting one or more outcomes for the new cells by applying a decision model to the features extracted from the new cell images, wherein the decision model is based on a description document that associates outcome metadata with features extracted from training images, wherein the training images and the new cell images are obtained using bright-field microscopy, wherein the new cells are oocytes or pronuclear embryos, and wherein the one or more outcomes include one or more of the following:
quality or reproductive potential of a new oocyte,
whether abnormalities in chromosome number are detected later in development,
whether genetic disorders are detected later in development, and
abnormal cell growth outcomes.

24. The system of claim 23 further comprising a microscopy system integrated with the one or more computing devices.

25. The system of claim 23, wherein the features extracted from the new cell images and the features extracted from the training images include one or more of the following:
a boundary of a polar body, measured manually or with image analysis using an edge detection algorithm;

an indication as to whether the polar body exists;
identification of inner and outer edges of a zona pellucida;
identification of perivitelline space;
a measurement of smoothness of the edges of the zona pellucida;
alignment of principal axes of the cytoplasm and the zona;
total area of the polar body, the zona pellucida, or the perivitelline space;
aspect ratio of the polar body, the zona pellucida, or the perivitelline space;
convexity of the boundary of the polar body, the zona pellucida, or the perivitelline space;
average image intensity of the polar body, the zona pellucida, or the perivitelline space;
standard deviation of the image intensity of the polar body, the zona pellucida, or the perivitelline space;
smoothness of the polar body, the zona pellucida, or the perivitelline space; and
subsampled image intensity or smoothness for grid areas within the polar body, the zona pellucida, or the perivitelline space.

26. The system of claim 23, wherein the features extracted from the new cell images and the features extracted from the training images include one or more of the following for a pronuclear embryo comprising pronuclei:
identification of the boundaries of the pronuclei, measured manually or with image analysis using an edge detection algorithm;
area of the pronuclei, measured individually and/or relative to each other;
aspect ratio of the pronuclei, measured individually and/or relative to each other;
convexity of a boundary of one or more of the pronuclei;
average image intensity of one or more of the pronuclei;
standard deviation of the image intensity of one or more of the pronuclei;
smoothness of one or more of the pronuclei; and
subsampled image intensity or smoothness for grid areas within one or more of the pronuclei.

27. The system of claim 23, wherein the quality or reproductive potential of the new oocyte is expressed as one or more of: a probability that the oocyte will fertilize when exposed to human sperm, a probability that a resulting embryo will reach a given stage of development, or a probability that the resulting embryo will result in a live birth when transferred to a uterus.

\* \* \* \* \*